US012194056B2

(12) United States Patent
Rossi et al.

(10) Patent No.: US 12,194,056 B2
(45) Date of Patent: *Jan. 14, 2025

(54) CCR7 APTAMERS AND USES THEREOF

(71) Applicant: CITY OF HOPE, Duarte, CA (US)

(72) Inventors: John J. Rossi, Azusa, CA (US); Jiehua Zhou, Monrovia, CA (US); Mayumi Takahashi, Pasadena, CA (US)

(73) Assignee: CITY OF HOPE, Duarte, CA (US)

( * ) Notice: Subject to any disclaimer, the term of this patent is extended or adjusted under 35 U.S.C. 154(b) by 855 days.

This patent is subject to a terminal disclaimer.

(21) Appl. No.: 17/319,391

(22) Filed: May 13, 2021

(65) Prior Publication Data

US 2021/0330692 A1    Oct. 28, 2021

Related U.S. Application Data

(63) Continuation of application No. 16/240,492, filed on Jan. 4, 2019, now Pat. No. 11,007,211.

(60) Provisional application No. 62/614,445, filed on Jan. 7, 2018.

(51) Int. Cl.
| | | |
|---|---|---|
| *C12N 15/115* | (2010.01) | |
| *A61K 9/00* | (2006.01) | |
| *A61K 31/7115* | (2006.01) | |
| *A61P 35/00* | (2006.01) | |

(52) U.S. Cl.
CPC ........ *A61K 31/7115* (2013.01); *A61K 9/0019* (2013.01); *A61P 35/00* (2018.01); *C12N 15/115* (2013.01); *C12N 2310/14* (2013.01); *C12N 2310/16* (2013.01); *C12N 2310/317* (2013.01); *C12N 2310/321* (2013.01); *C12N 2310/322* (2013.01); *C12N 2310/3519* (2013.01); *C12N 2320/32* (2013.01); *C12N 2320/51* (2013.01)

(58) Field of Classification Search
None
See application file for complete search history.

(56) References Cited

U.S. PATENT DOCUMENTS

| | | |
|---|---|---|
| 8,222,226 B2 | 7/2012 | Rossi et al. |
| 9,855,886 B2 | 1/2018 | Yamada |
| 2012/0082616 A1 | 4/2012 | Trawick et al. |
| 2014/0039042 A1 | 2/2014 | Toleikis et al. |
| 2014/0309287 A1 | 10/2014 | Rusconi et al. |
| 2016/0298113 A1 | 10/2016 | Saetrom |
| 2017/0218369 A1 | 8/2017 | Yang et al. |
| 2018/0078649 A1 | 3/2018 | Zu |

OTHER PUBLICATIONS

Dao, P. et al. "AptaTRACE elucidates RNA sequence-structure motifs from selection trends in HT-SELEX experiments" Cell Systems, Jul. 2016, 3, 62-70.

Darmostuk, M. et al. "Current approaches in SELEX: An update to aptamer selection technology" Biotechnology Advances, Nov. 2015, vol. 33, Issue 6, Part 2, pp. 1141-1161. Abstract Only.

Davey, R., Jr. et al. "HIV-1 and T cell dynamics after interruption of highly active antiretroviral therapy (HAART) in patients with a history of sustained viral suppression" PNAS 96, 15109-15114 (1999).

Ellington, A. et al. "In vitro selection of RNA molecules that bind specific ligands" Nature, Aug. 30, 1990; vol. 346, pp. 818-822.

Gijs, M. et al. "Aptamers as radiopharmaceuticals for nuclear imaging and therapy" Nuclear Medicine and Biology, vol. 43, Issue 4, Apr. 2016, pp. 253-271.—Abstract Only.

Guo, K. et al. "CELL-SELEX: Novel Perspectives of Aptamer-Based Therapeutics" International Journal of Molecular Sciences, 2008, vol. 9, pp. 668-678.

Hoinka, J. et al. "Large scale analysis of the mutational landscape in HT-SELEX improves aptamer discovery" Nucleic Acids Res 43, 5699-5707 (2015).

Iglesias-Ussel, M.D. et al. "HIV reservoirs: the new frontier" AIDS reviews 13, 13-29 (2011).

Keefe, A. et al. "Aptamers as therapeutics" Nature Reviews: Drug Discovery, Jul. 2010, vol. 9, pp. 537-550.

Lai, W.Y., et al., "A novel PD-L1-targeting antagonistic DNA aptamer with antitumor effects," Molecular Therapy—Nucleic Acids (2016) 5, e397, 9 pages.

Neff, C.P. et al. "An aptamer-siRNA chimera suppresses HIV-1 viral loads and protects from helper CD4(+) T cell decline in humanized mice" Science translational medicine 3, 66ra66 (2011).

Nozari, A., et al., "Aptamers for CD antigens: From cell profiling to activity modulation" Molecular Therapy: Nucleic Acids 6, 29-44 (2017).

Shao, K. et al. "Emulsion PCR: a high efficient way of PCR amplification of random DNA libraries in aptamer selection" PloS One 6, e24910 (2011). 7 pages.

Siliciano, J.D. et al. "Latency and viral persistence in HIV-1 infection" The Journal of clinical investigation 106, 823-825 (2000).

Sundaram, P. et al. "Therapeutic RNA aptamers in clinical trials" European Journal of Pharmaceutical Sciences, Jan. 2013, vol. 48, pp. 259-271. Abstract Only.

Takahashi, M. et al. "High throughput sequencing analysis of RNA libraries reveals the influences of initial library and PCR methods on SELEX efficiency" Scientific Reports, Sep. 2016. 14 pages.

(Continued)

*Primary Examiner* — Ekaterina Poliakova-Georgantas
(74) *Attorney, Agent, or Firm* — Perkins Coie LLP; Lara J. Dueppen; Adeh Vartanian

(57) ABSTRACT

Disclosed herein are CCR7 aptamers that specifically bind to and internalize into CCR7-expressing cells. The aptamers can be used as a therapeutic agent by itself or in combination with a small molecule by forming a conjugate with the small molecule. Targeted delivery of the small molecule can be achieved by such conjugates. Also disclosed are methods of treating a subject suffering from cancer by administering an effective amount of the aptamer or the aptamer-small molecule conjugate to the subject.

15 Claims, 12 Drawing Sheets
Specification includes a Sequence Listing.

(56) References Cited

OTHER PUBLICATIONS

Thiel, K. et al. "Delivery of chemo-sensitizing siRNAs to HER2+-breast cancer cells using RNA aptamers" Nucleic Acids Research, 2012, vol. 40, No. 3, pp. 6319-6337.

Tuerk, C. et al. "Systematic Evolution of Ligands by Exponential Enrichment: RNA Ligands to Bacteriophage T4 DNA Polymerase" Science, Aug. 1990, vol. 249, pp. 505-510.

Yu, Y. et al. "Molecular selection, modification and development of therapeutic oligonucleotide aptamers" International Journal of Molecular Sciences, 2016, vol. 17. 19 pages.

Yufa, R. et al. "Emulsion PCR significantly improves nonequilibrium capillary electrophoresis of equilibrium mixtures-based aptamer selection: allowing for efficient and rapid selection of aptamer to unmodified ABH2 protein" Analytical chemistry 87, 1411-1419 (2015).

Zhou, J. et al. "Cell-Specific RNA Aptamer against Human CCR5 Specifically Targets HIV-1 Susceptible Cells and Inhibits HIV-1 Infectivity" Chemistry & biology 22, 379-390 (2015).

Zhou, J., et al. "Novel dual inhibitory function aptamer-siRNA delivery system for HIV-1 therapy" Mol Ther 16, 1481-1489 (2008).

Zhou, J. et al. "Functional In Vivo Delivery of Multiplexed Anti-HIV-1 siRNAs via a Chemically Synthesized Aptamer With a Sticky Bridge" Mol Ther 21, 192-200 (2013).

Zhou, J. et al. "Cell-type-specific, Aptamer-functionalized Agents for Targeted Disease Therapy" Molecular Therapy: Nucleic Acids, 2014, vol. 3, 17 pages.

Zhou, J. et al. "Selection, characterization and application of new RNA HIV gp 120 aptamers for facile delivery of Dicer substrate siRNAs into HIV infected cells" Nucleic Acids Res (2009).

Zhou, J. et al. "Cell-specific aptamer-mediated targeted drug delivery" Oligonucleotides 21, 1-10 (2011).

CCR7 APTAMERS AND USES THEREOF

CROSS-REFERENCE TO RELATED APPLICATIONS

This application is a continuation of U.S. patent application Ser. No. 16/240,492, filed Jan. 4, 2019, which claims the benefit of U.S. provisional Patent Application No. 62/614,445, filed Jan. 7, 2018, both of which are incorporated herein by reference in their entirety, including drawings.

STATEMENT REGARDING FEDERALLY SPONSORED RESEARCH

This invention was made with government support under R01 A1029329, P30 CA033572, and R01 A1042552 awarded by the National Institutes of Health. The government has certain rights in the invention.

SEQUENCE LISTING

This application contains a Sequence Listing, which is submitted in ASCII format via PatentCenter, and is hereby incorporated by reference in its entirety. The ASCII copy, created on Apr. 18, 2024, is named SubstituteSequenceListing.txt and is 2 KB in size.

BACKGROUND

It has been challenging to develop aptamer-based therapeutics due to nuclease degradation. The half-life of an unmodified nucleic acid is very short, less than 10 minutes. Therefore, a need exists to develop targeted therapy as an effective and safe treatment for various diseases and conditions such as cancer. This disclosure satisfies the need in the art.

SUMMARY

The invention described herein relates to high-affinity CCR7 aptamers. In some embodiments, the aptamer is a nucleic acid aptamer, such as an RNA aptamer. In some embodiments, the aptamer is used as a therapeutic agent targeting cancer cells expressing CCR7. In other embodiments, the aptamer is used as a delivery vehicle by conjugating to a small molecule such that the small molecule is specifically delivered to the desired cell type expressing CCR7. In some embodiments, the small molecule is non-covalently conjugated to the CCR7 aptamer. In some embodiments, the small molecule includes saRNA, siRNA, shRNA or other microRNAs, a toxin, a chemotherapeutic agent, or another aptamer. In some embodiments, the aptamer is conjugated to a small molecule via one or more linkers, and/or a sticky-bridge comprising a complementary sequence. The linker can be a nucleotide linker or a polycarbon linker. In some embodiments, the aptamer, whether used as a therapeutic agent alone or used as a delivery vehicle by conjugation to a small molecule, may be chemically modified such that the half-life, stability, and/or binding affinity of the aptamer are improved.

In some embodiments, the CCR7 aptamer disclosed herein can be conjugated to one or more aptamers, such as a PD-1 aptamer, a PD-L1 aptamer, and a CD8 aptamer to generate a bi-specific aptamer conjugate, a multi-specific aptamer conjugate, or MATE.

In another aspect, methods for treating a cancer patient are provided. Such methods include administering a therapeutically effective amount of a therapeutic composition, the therapeutic composition comprising an aptamer that specifically binds to CCR7, a CCR7 aptamer conjugated to a small molecule, a bi-specific aptamer, a multi-specific aptamer, or MATE as described herein.

DETAILED DESCRIPTION

Cell type-specific aptamers that selectively bind human CCR7 protein, systems for cell type-specific delivery of small molecules and methods for their use are provided herein. According to the embodiments described herein, the cell type-specific aptamers can be used as effective RNA-based targeted cancer therapies. In addition to their utility as stand-alone therapeutics, cell type-specific aptamers can also serve as a new therapeutic modality by functioning as a delivery vehicle for another therapeutic. Thus, cell-type specific aptamer-based nano-conjugates for targeted cancer therapy are also disclosed herein.

Cell Type-Specific Aptamers

Aptamers[1,2], often termed "chemical antibodies," are short, single-stranded (ss) DNA or RNA molecules that bind to a specific target. They are typically selected through systematic enrichment of ligands by exponential enrichment (SELEX) technology[3]. Aptamers are functionally comparable to antibodies, but possess many additional attractive features, including relatively small physical size (nanoscale), flexible structure, quick chemical production, versatile chemical modification, high stability, and lack of immunogenicity. As such, they show increasing potential for therapeutic applications[4,5]. Aptamers can serve as direct antagonists for blocking the interaction of disease-associated targets, or as target-specific carriers for delivering other therapeutic agents (e.g. siRNA, shRNA, microRNA, other aptamers, chemotherapeutics, or toxins)[6].

Figure 1:
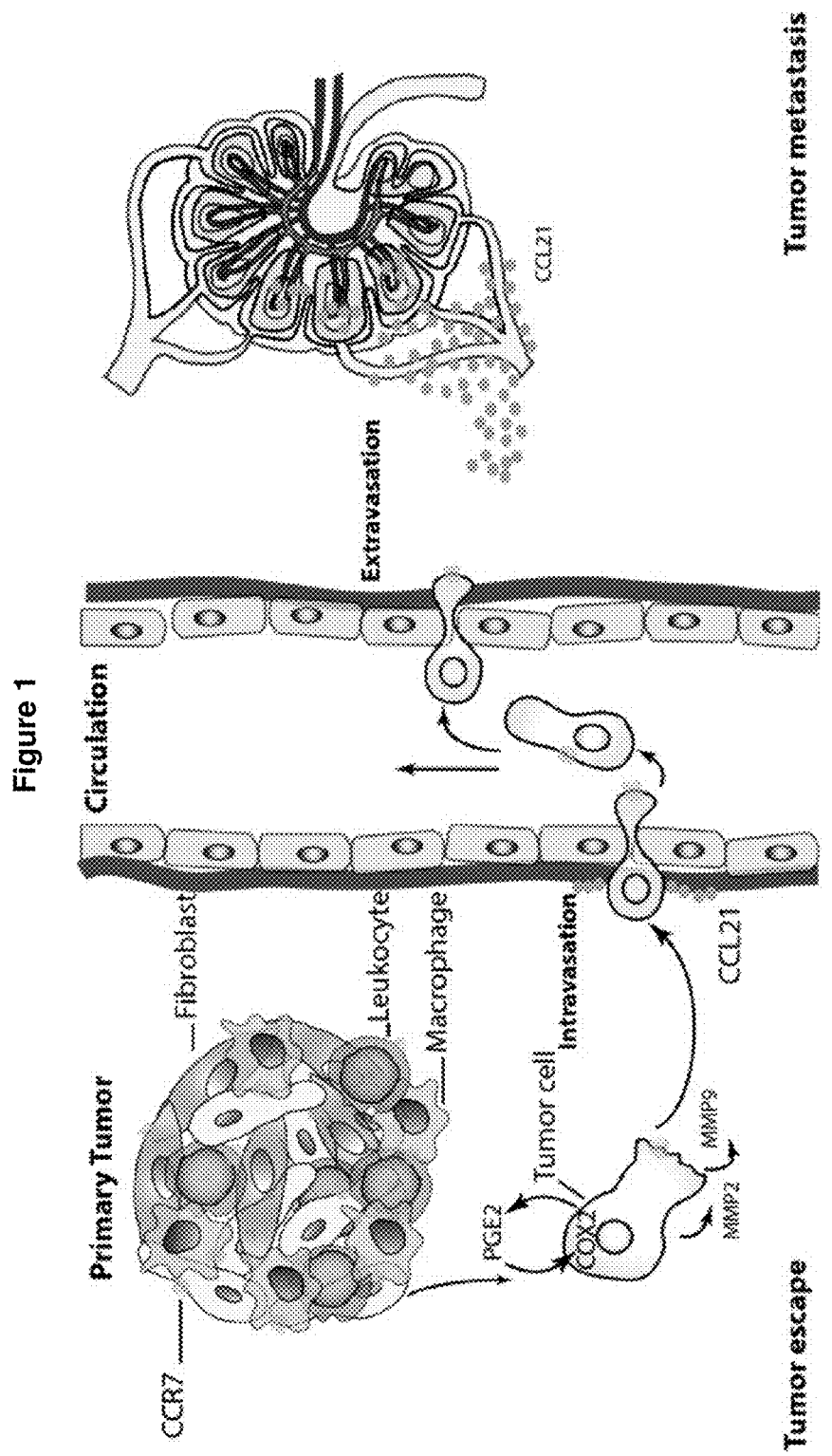
FIG. 1 illustrates CCR7's central roles in tumor cell dissemination, migration and metastasis formation. CCL21 promotes migration and invasion of cancer cells via CCR7.

Human CC chemokine receptor 7 (CCR7), a member of the G protein-coupled receptor family, is known to control migration of memory T-cells to inflamed organs, such as lymph node. CCR7 is expressed by various cancer cells, such as breast cancer, melanoma, non-small cell lung cancer, prostate cancer, chronic lymphocytic leukemia (CLL), non-Hodgkin's lymphoma (NHL), T-cell leukemia, etc. Expression of CCR7 by cancer cells is linked to metastasis to lymph node. The signal transduction pathways triggered by CCR7 engagement through its ligands, the chemokines CCL19 and CCL21, represent a promising target for cancer therapy. Thus, CCR7 is a convenient target for aptamers and their conjugates. FIG. 1 illustrates CCR7's central roles in tumor cell dissemination, migration and metastasis formation.

Disclosed herein are high-affinity CCR7 aptamers that are capable of selectively binding to CCR7-expressing cells and being internalized specifically into CCR7-expressing cells, as well as methods and assays for screening and identifying such aptamers having high affinity for CCR7. The therapeutic aptamers disclosed herein, either used alone or in combination with small molecules, can specifically target CCR7-expressing cancer cells and improve tumor suppression.

In one embodiment, aptamers for targeting certain cell types, such as CCR7-expressing tumor cells, are provided as a cancer therapy for breast cancer, melanoma, non-small cell lung cancer, prostate cancer, chronic lymphocytic leukemia (CLL), non-Hodgkin's lymphoma (NHL), T-cell leukemia, etc. An "aptamer" is any suitable small molecule, such as a nucleic acid or a peptide molecule that binds specifically to a target, such as a small molecule, protein, nucleic acid, cell, tissue or organism. Aptamers that target specific cell surface proteins can be employed as delivery molecules to target a distinct cell type, thereby reducing off-target effects or other unwanted side effects. Further, by binding a specific cell surface protein, the aptamers may also be used as therapeutic agents on their own.

In some embodiments, the therapeutic effects of the disclosed aptamers can be improved by developing bivalent aptamer conjugates to achieve higher avidity to the target. In certain embodiments, conjugation can be optimized by varying the length and/or sequence of the linker or sticky bridge such that the correct structure of the selected aptamers and the activity of therapeutic agents can be maximally retained. In some embodiments, the linker, e.g., a polycarbon linker, has a length of between 3 units and 10 units, each unit having 3 carbons. In some embodiments, the sticky bridge has a GC-rich sequence. In some embodiments, the sticky bridge has a length of between 5 bp and 30 bp. In some embodiments, the sticky bridge has a length of 5 bp, 6 bp, 7, bp, 8 bp, 9 bp, 10 bp, 11 bp, 12 bp, 13 bp, 14 bp, 15 bp, 16 bp, 17 bp, 18 bp, 19 bp, 20 bp, 21 bp, 22 bp, 23 bp, 24 bp, 25 bp, 26 bp, 27 bp, 28 bp, 29 bp, or 30 bp. Additionally, two nano-conjugates can be combined to further improve the targeting and therapeutic effects. For example, combinational use of various RNA therapeutics can achieve synergistic effects.

Figure 2:
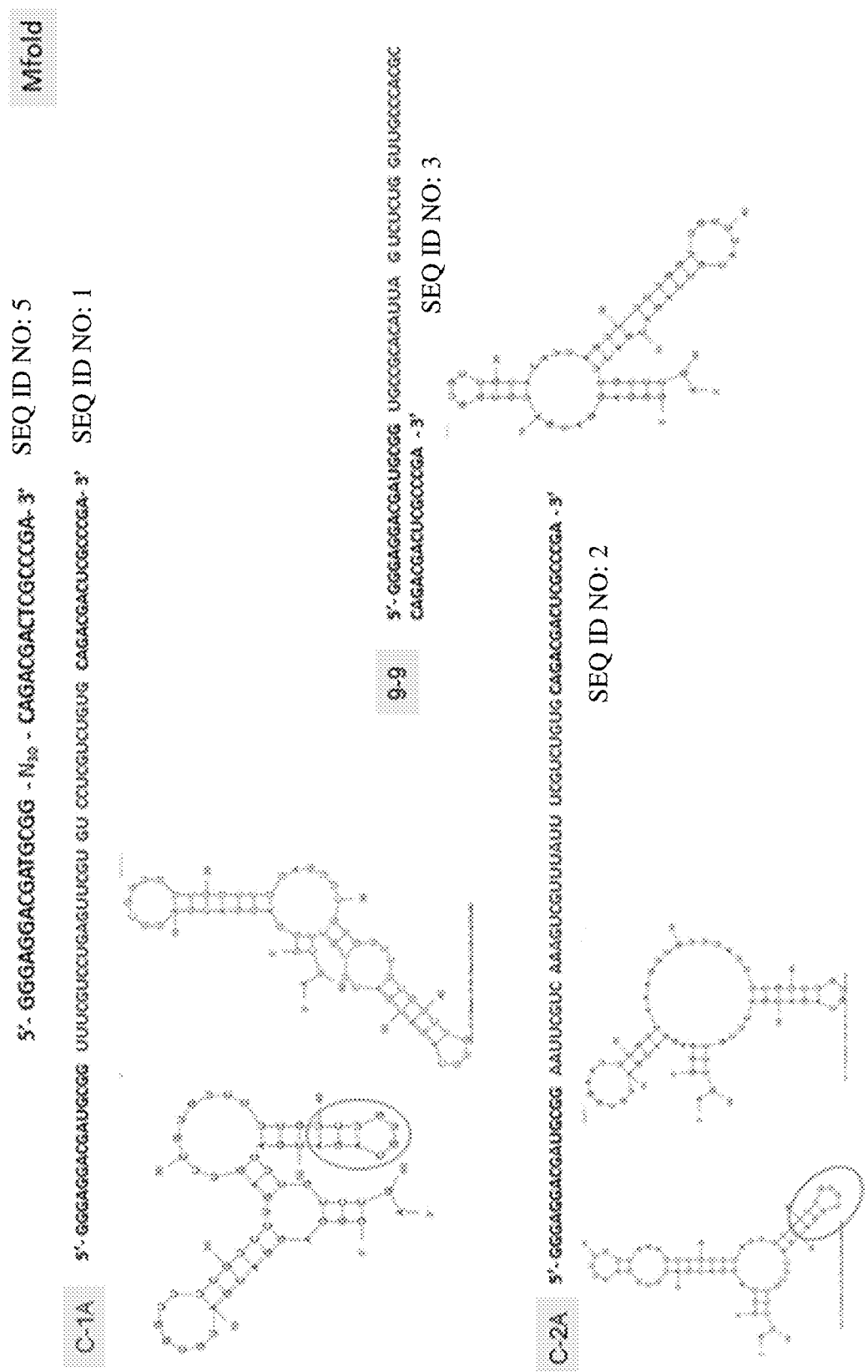
FIG. 2 illustrates M-fold of examples of CCR7 aptamers.
Figure 3:
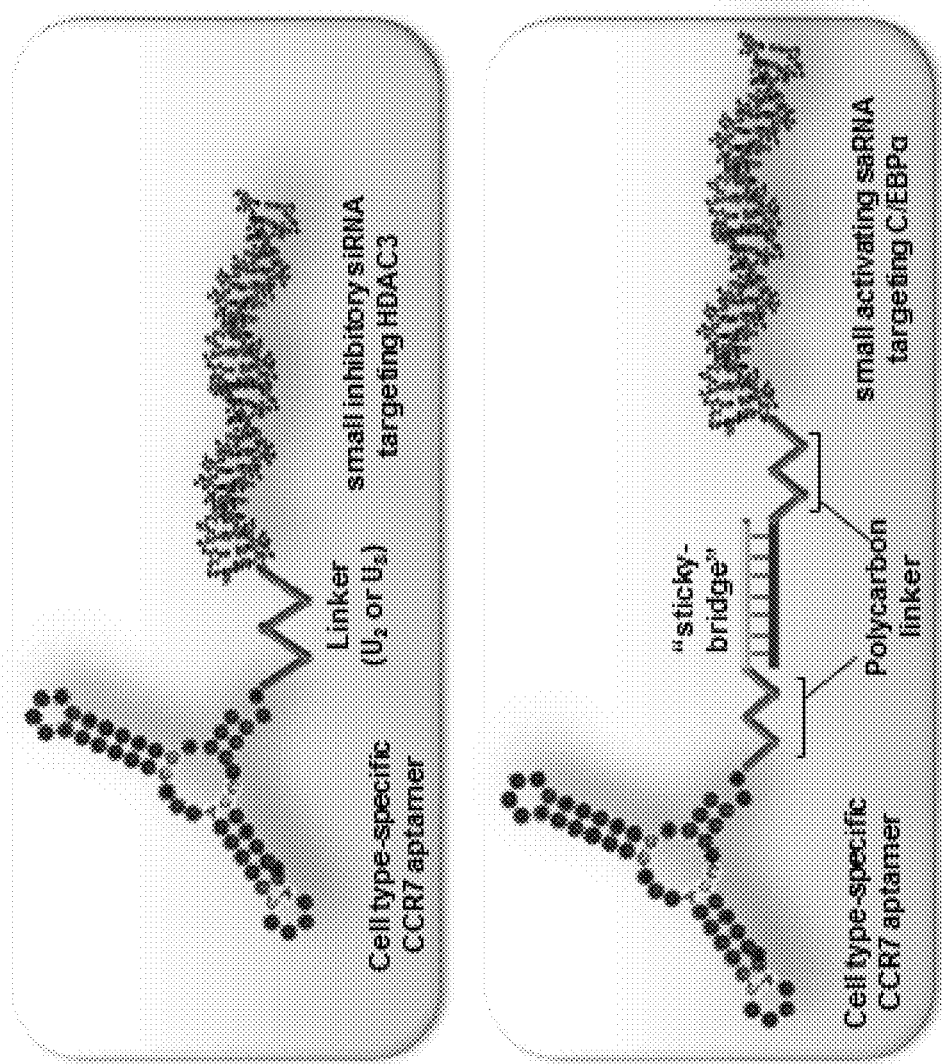
FIG. 3 illustrates examples of CCR7 aptamer-small molecule conjugates using different linkers. Examples of small molecules include HDAC3 siRNA and CCR7 aptamer-C/EBPα saRNA.

Therefore, in some embodiments, a cell-type specific aptamer that targets and binds CCR7 is provided. In one embodiment, the aptamer is a nucleic acid molecule. For example, the nucleic acid CCR7 aptamer can be an RNA aptamer molecule. FIG. 2 shows M-fold of some examples of the aptamers disclosed herein. The CCR7 aptamers share the same 5' and 3' fixed regions. The core sequences (underlined) of these aptamers are different.

C-1A aptamer:
(SEQ ID NO: 1)
5'-GGGAGGACGAUGCGG<u>UUUCGUCCUGAGUUCGUGUCCUCGUCUGUGC</u>AG
ACGACUCGCCCGA-3'

C-2A aptamer:
(SEQ ID NO: 2)
5'-GGGAGGACGAUGCGG<u>AAUUCGUCAAAGUCGUUUAUUUCGUCUGUGC</u>AG
ACGACUCGCCCGA-3'

DD9-9 aptamer:
(SEQ ID NO: 3)
5'-GGGAGGACGAUGCGG<u>UGCCGCACAUUAGUCUCUGGUUGCCCACGC</u>CAG
ACGACUCGCCCGA-3'

C-6 aptamer:
(SEQ ID NO: 4)
5'-GGGAGGACGAUGCGG<u>UCCAUCGUCUCUUAUCGUCUCUUGUCGCGC</u>CAG
ACGACUCGCCCGA-3'

Nucleic acid aptamers with binding affinities in nanomolar range have been utilized for flexible applications ranging from diagnostic to therapeutic assay formats. Moreover, aptamers that target CCR7 are employed as delivery molecules to target a distinct cell type, e.g., tumor cells, hence reducing off-target effects or other unwanted side effects.

Selection and Characterization of CCR7 RNA Aptamers

In some embodiments, disclosed herein are methods of identifying RNA aptamers directed to human CCR7. The method includes synthesizing representative aptamers for further characterization and determining their binding affinity, target specificity, and ability to be internalized within cells expressing CCR7. The method further includes assessing which CCR7 aptamers functionally antagonize CCR7 activities.

Selection of aptamers may be accomplished by an optimized protocol for in vitro selection, known as SELEX (Systemic Evolution of Ligands by Exponential enrichment). Although the SELEX process has been established as a general technique for aptamer selection, it is not predictable nor is it standardized for use with any target. Instead, the SELEX process must be optimized and customized for each particular target molecule. Each SELEX experiment includes its own challenges and is not guaranteed to work for all targets.

Many factors are important for successful aptamer selection. For example, the target molecule should be stable and easily reproduced for each round of SELEX, because the SELEX process involves multiple rounds of binding, selection, and amplification to enrich the nucleic acid molecules. In addition, the nucleic acids that exhibit specific binding to the target molecule have to be present in the initial library. Thus, it is advantageous to produce a highly diverse nucleic acid pool. Because the starting library is not guaranteed to contain aptamers to the target molecule, the SELEX process for a single target may need to be repeated with different starting libraries. Aptamer selection using SELEX is unpredictable. Even when all of the factors are optimized for successful aptamer selection, the SELEX process does not always yield viable aptamers for every target molecule.

As described herein, a well-established "Live cell-based SELEX" strategy[7] is combined with high throughput sequencing (HTS) technology and bioinformatics analysis to identify new 2'-fluoropyrimidine modified CCR7 RNA aptamers that are capable of specifically targeting the CCR7-expressing cells. Hela cells that stably over-express CCR7 can be used. Selected CCR7 aptamers bind specifically and are internalized into the CCR7-expressing Hela cells. In some embodiments, seven selection rounds containing both positive and negative selection are performed with cell-specific binding and internalization of the RNA libraries. Barcode-based Illumina deep sequencing technology can be used to identify the individual aptamer sequences for the RNA pools from selection rounds 0-7. During SELEX procedures, a specific enrichment was observed.

Modification of Aptamers

To increase the half-life, stability and/or binding affinity of aptamers, particularly nucleic acid aptamers, the selected aptamers are chemically modified, for example, by replacing the 2' position with either a fluoro-(F), amino-($NH_2$), or O-methyl ($OCH_3$) group, and by capping the 3' end with inverted thymidine to increase nuclease resistance while also enhancing binding affinity. The aptamers can be modified in-SELEX and/or post-SELEX.

For in-SELEX modifications, aptamers with the desired modifications are directly isolated from a DNA or RNA library containing modified nucleotides that are compatible with DNA or RNA polymerases. The aptamers that can be modified by this method include 2'-aminopyrimidines, 2'-fluoropyrimidines, 2'-O-methyl nucleotides and locked nucleic acids (LNA).

As for post-SELEX modifications, different modifications at various positions (e.g., base, 2'-position, sugar ring, phosphate group) can be introduced to selected aptamers during solid-phase chemical synthesis. Since the affinity/specificity and function of an aptamer depend on its structure, post-SELEX modification may affect the inherent properties and folding structures of the original aptamers, thereby compromising the binding affinity. Therefore, it is necessary to precisely tailor modifications to optimize the desired functions.

Various chemical modifications to stabilize aptamers are disclosed in the art, for example, Gijs M., et al., *Nuclear Medicine and Biology*, 43 (4): 253-271 (2016); and Yu Y, et al. *International Journal of Molecular Sciences*, 17 (3): 358 (2016).

Cell Type-Specific Aptamer-Based Nano-Conjugates

Disclosed are cell type-specific aptamer-based small RNA nano-conjugates for targeted cancer therapy. These cell type-specific CCR7 aptamers bind and selectively enter into the cells expression CCR7. Various small RNAs, e.g., siRNAs and saRNAs, can be conjugated to the CCR7 aptamer, and these conjugates can be used to accommodate target genetic changes. Thus, these cell-specific, internalizing RNA aptamers can be used for cell type-specific gene silencing or activation for targeted treatment of CCR7-expressing cancers.

Engineering various aptamer-based nano-conjugates using a non-covalent conjugation approach is disclosed herein. In some embodiments, cell-type-specific aptamer-based nano-conjugates can be used to deliver small molecules such as functional nucleic acids into CCR7-expressing tumor cells. Some examples of the nano-conjugates include but are not limited to aptamer-small activating RNA (saRNA) conjugates, and aptamer-siRNA conjugates. The nano-conjugates disclosed herein are efficacious in suppressing tumors growth through specifically targeting to CCR7 expressing cancer cells. The effect of the aptamer-based nano-conjugates is determined based on the specificity of delivery, targeted gene regulation, and inhibition of tumor cell proliferation.

In some embodiments, a selected aptamer can be linked to a small molecule through a complementary "sticky sequence" or "sticky bridge" to generate an aptamer-small molecule conjugate.

To determine which conjugates specifically bind and are internalized into target cells, flow cytometry and live-cell confocal microscopy experiments can be performed as described above. The binding affinity test is performed using cell lines expressing target protein as well as primary cells.

Thus, in addition to their utility as stand-alone therapeutics, aptamers disclosed herein can be used as escorts for another therapeutics by forming a conjugate of a cell type-specific aptamer and a small molecule therapeutic agent. Such small molecule therapeutic agents include but are not limited to, for example, saRNA, SiRNA, shRNA, microRNA, anti-miR, a therapeutic aptamer, a chemotherapeutic, a toxin, a radioisotope, an antisense oligonucleotides, a photoactive agent, and a dye.

The small molecule that is conjugated to the aptamers disclosed herein may include any suitable short RNA structure including, but not limited to, siRNAs, shRNAs, miRNAs and other short dsRNAs. In one embodiment, the siRNA molecule may be a traditional monofunctional siRNA molecule having a functional antisense strand and a complementary sense strand. In some embodiments, known anti-cancer siRNA molecules, such as siRNAs targeting histone deacetylase 3 (HDAC3) or CCAAT/enhancer-binding protein-α (C/EBPα) can be used.

HDAC3 (histone deacetylase 3) is essential for efficient DNA replication and DNA damage control, which was found to be highly expressed in various tumors, such as renal cell cancer, colorectal and gastric cancer as well as in classical Hodgkin's lymphoma. siRNA-mediated knockdown of HDAC3 in Hela cells results in inhibition of cell proliferation.

C/EBPα (CCAAT/enhancer-binding protein-α) is a transcriptional regulator that plays an essential role in tumor metastasis. saRNA-mediated enhanced C/EBPα expression can reduce tumor burden and metastasis.

In another embodiment, the aptamer-small molecule conjugate is constructed by a method of non-covalent conjugation. Non-covalent conjugation involves chemically linking two molecules without sharing of pairs of electrons. Non-covalent conjugation may involve electrostatic interactions such as hydrogen bonds, ionic bonds, van der Waals forces and hydrophobic interactions.

Multi-Specific Aptamer Conjugates

Figure 4:
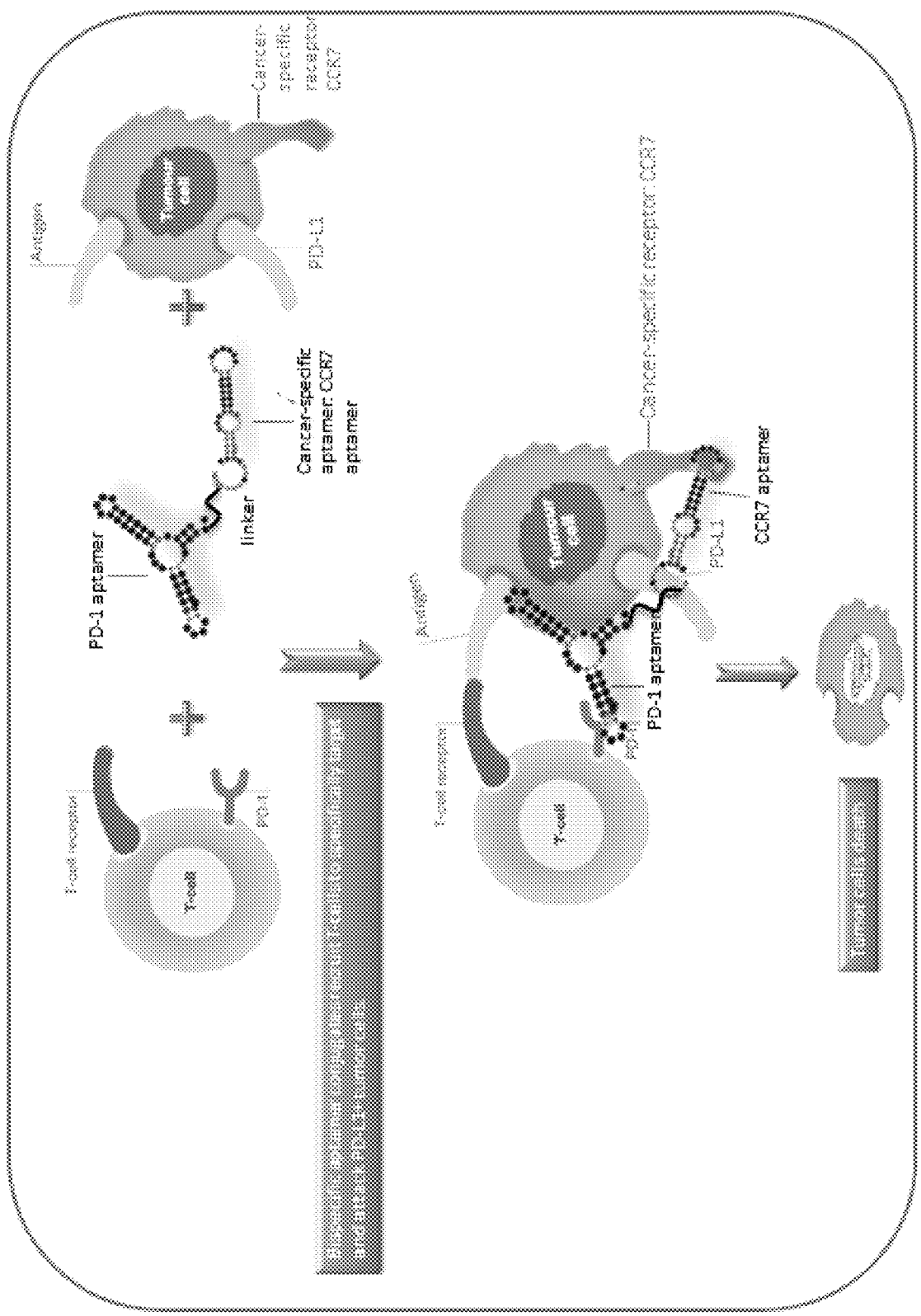
FIG. 4 illustrates that CCR7 aptamers can be used as antagonists/delivery agents in a bi-specific aptamer system-induced T-cells to attack cancer cells and prevent T-cells deactivation.
Figure 5:
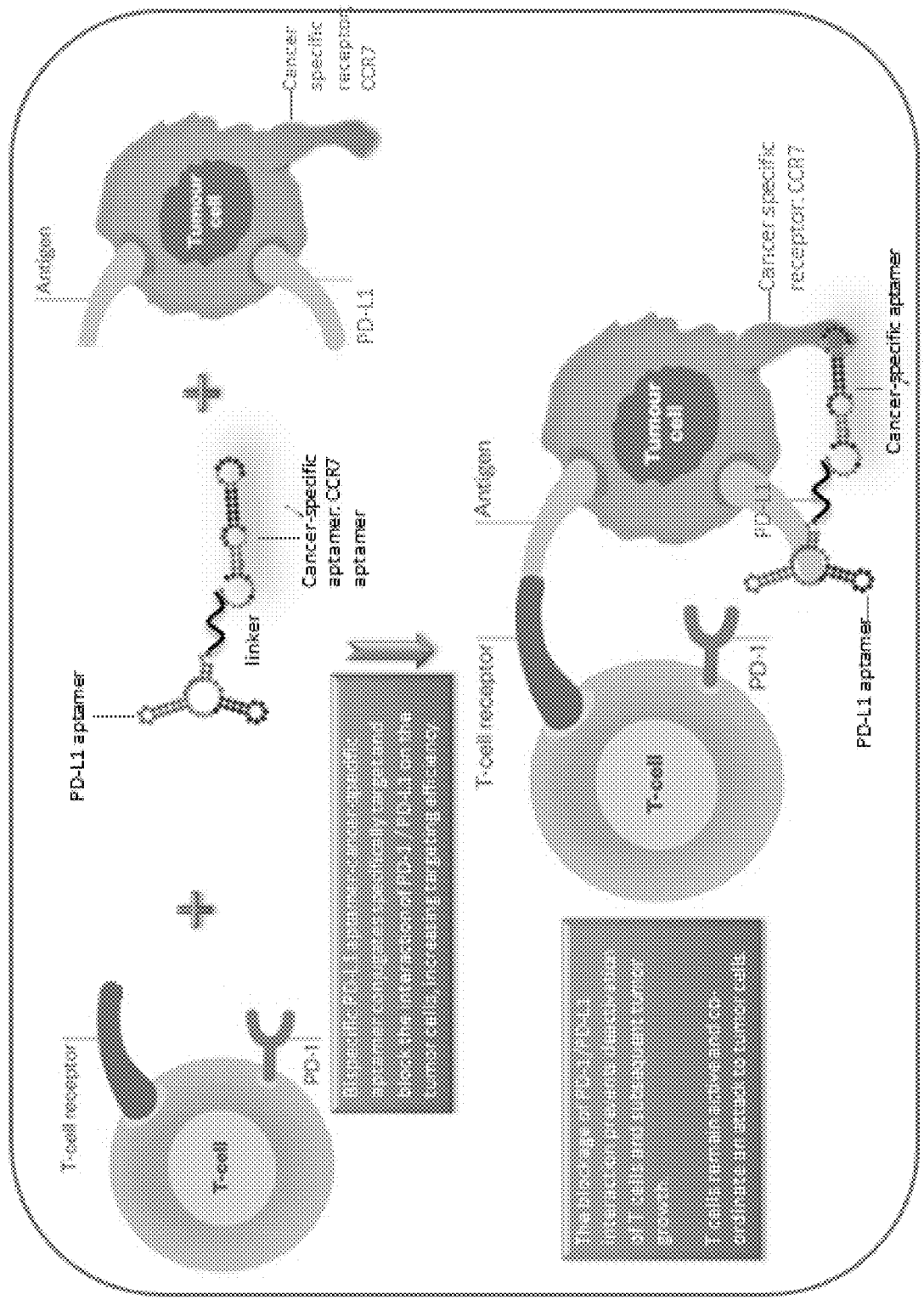
FIG. 5 illustrates that CCR7 aptamers can be used as antagonists to generate bi-specific aptamers to increase targeting efficiency.

In some embodiments, two or more aptamers can be conjugated via any of the linkers disclosed herein or via non-covalent conjugation to generate bi-specific or multi-specific aptamer conjugates. For example, the CCR7 aptamer disclosed herein can be conjugated to a PD-1 aptamer to form a bi-specific aptamer conjugate, which can induce T-cells to attack cancer cells and prevent T-cells deactivation, as illustrated in FIG. 4. In another example, the CCR7 aptamer disclosed herein can be conjugated to a PD-L1 aptamer to form a bi-specific aptamer conjugate, which can increase targeting efficiency, as illustrated in FIG. 5.

It has been demonstrated that conjugating cell-specific aptamers to therapeutic agents can facilitate specific recognition and intracellular internalization to the targeted cells, thereby improving the local concentration of the drugs and their therapeutic efficacy. A bi-specific aptamer conjugate consisting of high-affinity aptamers against c-Met and CD16 specifically recruited NK (natural killer) cells to c-Met-overexpressing tumor cells, consequently inducing tumor cell lysis. Thus, also disclosed herein are cell-specific aptamers that possess high binding affinity and exquisite specificity to engage CD8+ T cells to target CCR7-expressing tumor cells and induce CD8+ T cell-dependent killing.

Figure 6:
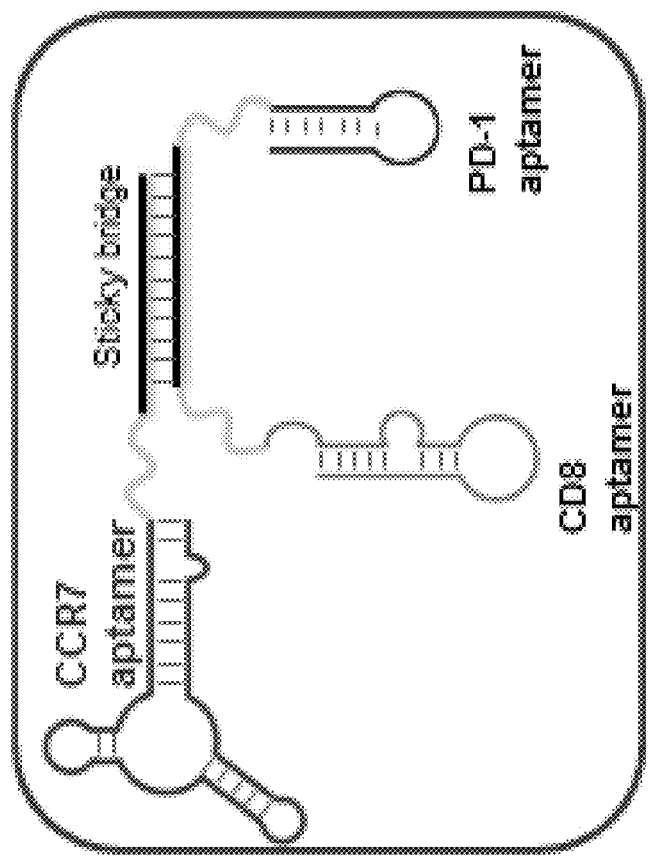
FIG. 6 illustrates an example of MATE, including a CCR7 aptamer, which identifies CCR7 expressing cancer cells; a PD-1 aptamer, which blocks PD-1/PD-L1 signaling and identifies CD8+ T cells; and a CD8 aptamer, which identifies CD8+ T cells.
Figure 7:
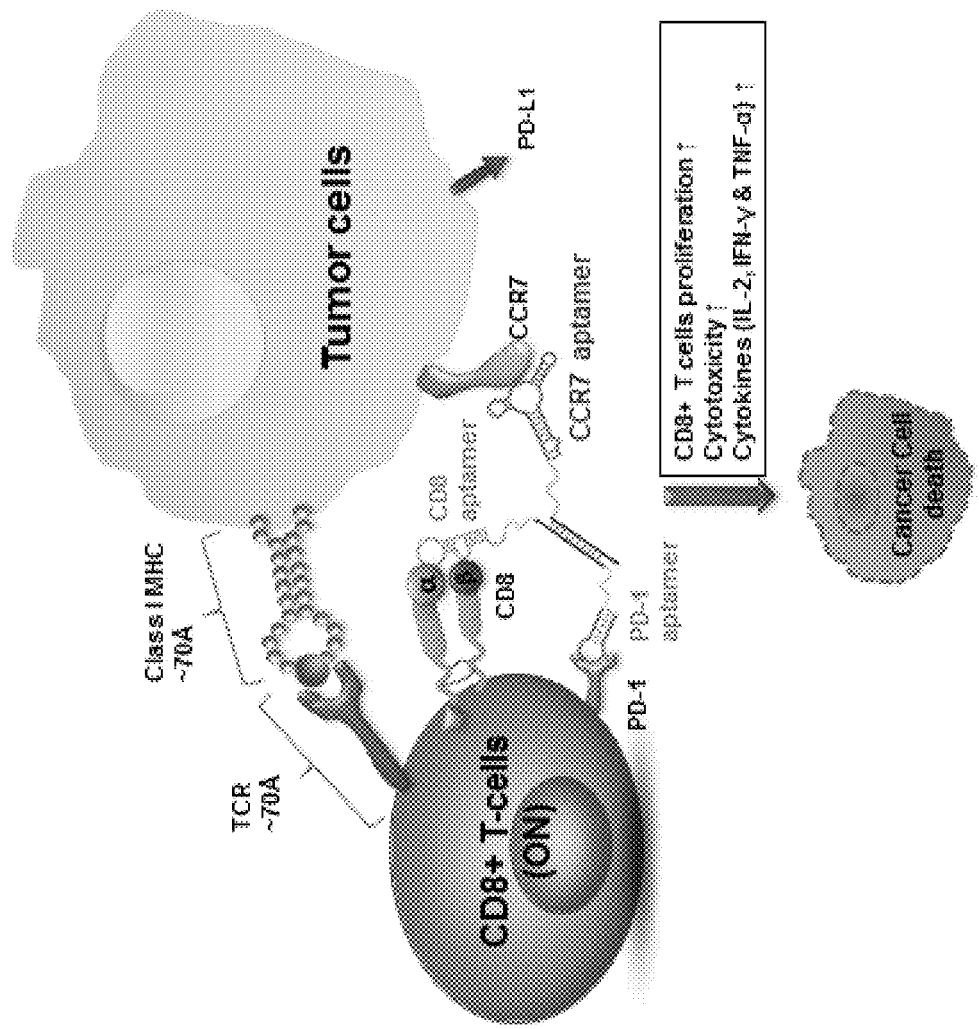
FIG. 7 illustrates targeting cancer by CCR7-MATE. ON: active CD8+ T cells; TCR: T cell receptor; MHC: major histocompatibility complex.

In some embodiments, disclosed herein is a Multi-specific Aptamers-based T cells Engager (MATE: CD8/PD-1/CCR7) (see FIG. 6). The MATE simultaneously binds and engages CD8+ T cells (via CD8 and PD-1) and tumor cells (via CCR7) and drives killer T cells to eliminate CCR7-expressing tumor cells, as illustrated in FIG. 7. As shown in the figures, a MATE containing three aptamers specific to CD8, PD-1 and CCR7 functions as a bridge to engage CD8+ T cells (CD8+/PD-1+) and tumor cells (CCR7+) to induce special cytotoxicity.

Treatment of Cancer

The CCR7 aptamers, the aptamer-small molecule conjugates, bi-specific or multi-specific aptamer conjugates, and MATE described herein can be used for specifically targeting CCR7-expressing cells as well as a therapy for cancer. Therefore, methods for treating a subject suffering from various cancer are provided according to the embodiments described herein.

"Treating" or "treatment" of a disease or a condition may refer to preventing the disease or condition, slowing the onset or rate of development of the disease or condition, reducing the risk of developing the disease or condition, preventing or delaying the development of symptoms associated with the disease or condition, reducing or ending symptoms associated with the disease or condition, generating a complete or partial regression of the disease or condition, or some combinations thereof.

The method for treating a cancer includes administering a therapeutically effective amount of a therapeutic composition. An "effective amount," "therapeutically effective amount" or "effective dose" is an amount of a composition (e.g., a therapeutic composition or agent) that produces a desired therapeutic effect in a subject, such as preventing or treating the cancer or alleviating symptoms associated with the cancer. The precise therapeutically effective amount is an amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. For additional guidance, see Remington: The Science and Practice of Pharmacy 21$^{st}$ Edition, Univ. of Sciences in Philadelphia (USIP), Lippincott Williams & Wilkins, Philadelphia, PA, 2005.

The therapeutic composition may include, among other things, an aptamer, and/or an aptamer-small molecule conjugate described herein. For example, in some embodiments, an RNA aptamer that may be part of the therapeutic composition.

The therapeutic composition may also include one or more pharmaceutically acceptable carriers. A "pharmaceutically acceptable carrier" refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or some combination thereof. Each component of the carrier must be "pharmaceutically acceptable" in that it must be compatible with the other ingredients of the formulation. It also must be suitable for contact with any tissue, organ, or portion of the body that it may encounter, meaning that it must not carry a risk of toxicity, irritation, allergic response, immunogenicity, or any other complication that excessively outweighs its therapeutic benefits.

The therapeutic compositions described herein may be administered by any suitable route of administration. A route of administration may refer to any administration pathway known in the art, including but not limited to aerosol, enteral, nasal, ophthalmic, oral, parenteral, rectal, transdermal (e.g., topical cream or ointment, patch), or vaginal. "Transdermal" administration may be accomplished using a topical cream or ointment or by means of a transdermal patch. "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. In some embodiments, the therapeutic compositions described herein are administered by intravenous injection or intraperitoneal injection.

Having described the invention with reference to the embodiments and illustrative examples, those in the art may appreciate modifications to the invention as described and illustrated that do not depart from the spirit and scope of the invention as disclosed in the specification. The examples are set forth to aid in understanding the invention but are not intended to, and should not be construed to limit its scope in any way. The examples do not include detailed descriptions of conventional methods. Such methods are well known to those of ordinary skill in the art and are described in numerous publications. Further, all references cited above and in the examples below are hereby incorporated by reference in their entirety, as if fully set forth herein.

EXAMPLES

Example 1: Binding and Internalization of CCR7 Aptamers

This example demonstrates that CCR7 aptamers selectively bind to CCR7-expressing cells and are internalized specifically into CCR7-expressing cells.

As shown in Table 1, CCR7 aptamers demonstrated high binding affinity to CCR7-positive Hela cells, CCR7-positive H9 cells, and CCR7-positive human memory CD4+ T cells.

TABLE 1

Binding Affinity of CCR7 Aptamers

| Candidate CCR7 aptamers | As analyzed by flow cytometry analysis (CCR7-positive cells) | | | As analyzed by gel shift assay Recombinant CCR7 protein |
|---|---|---|---|---|
| | HeLa-CCR7 positive cells | H9-CCR7 positive cells | Human memory CD4+ T cells (CCR7 positive) | |
| C-1A | +++ | +++ | ++ | ++ |
| C-2A | +++ | +++ | ++ | +++ |
| C-5B | + | +++ | + | + |
| C-6 | ++ | ++ | + | + |

Figure 8:
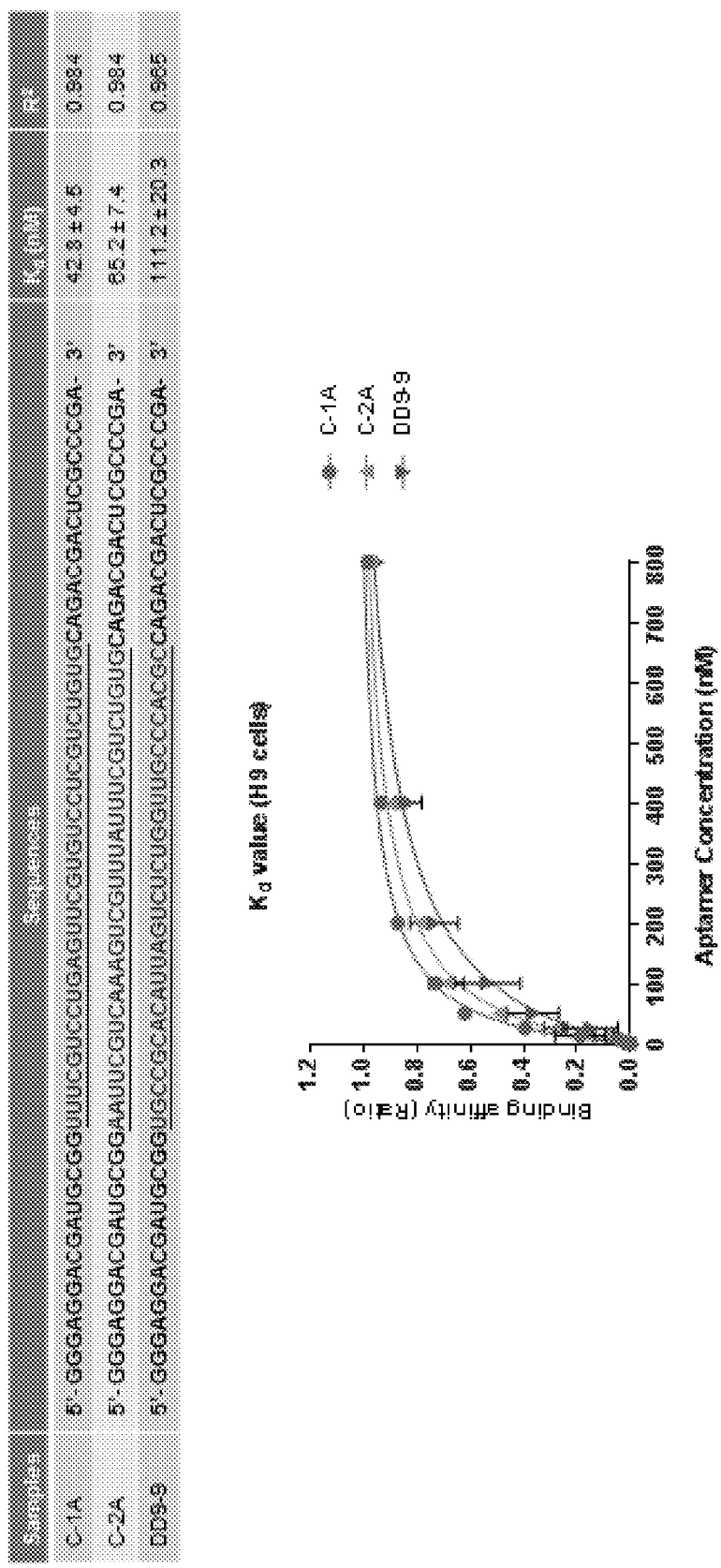
FIG. 8 illustrates binding affinity ($K_d$) of additional examples of CCR7 aptamers such as C-1A and C-2A (SEQ ID NOS: 1-3).

+++: >50% binding affinity
++: 30-50% binding affinity
+: 10-25% binding affinity As shown in FIG. 8, binding affinity of CCR7 aptamers was dose-dependent and CCR7 aptamer C-1A demonstrated the highest binding affinity.

Figure 9:
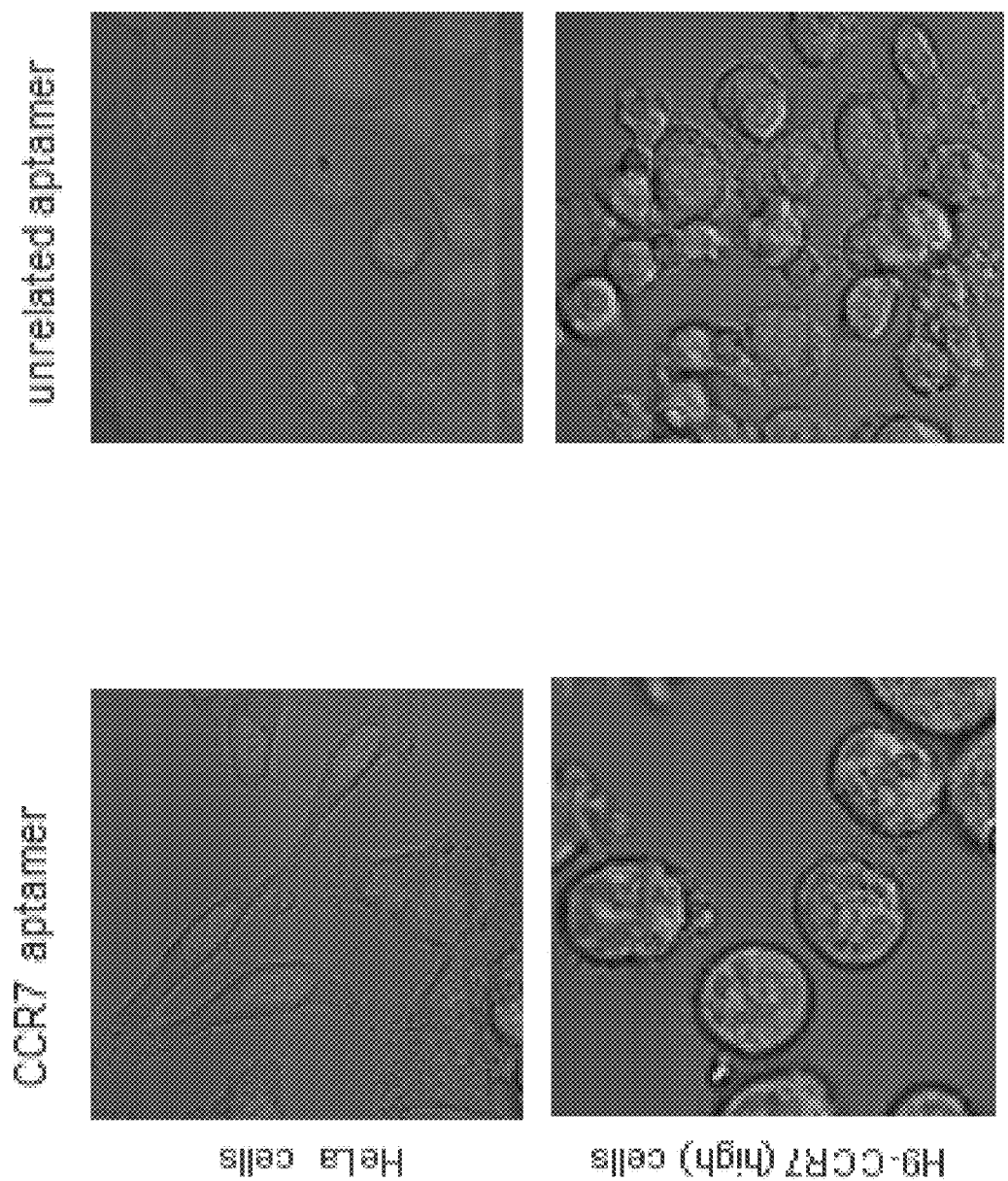
FIG. 9 shows internalization of CCR7 aptamers into CCR7-expressing cells.

As shown in FIG. 9, CCR7 aptamers were internalized specifically into CCR7-expressing cells.

Example 2: Gene Silencing Effects of CCR7 Aptamer-Small RNA Nano-Conjugates

Figure 10:
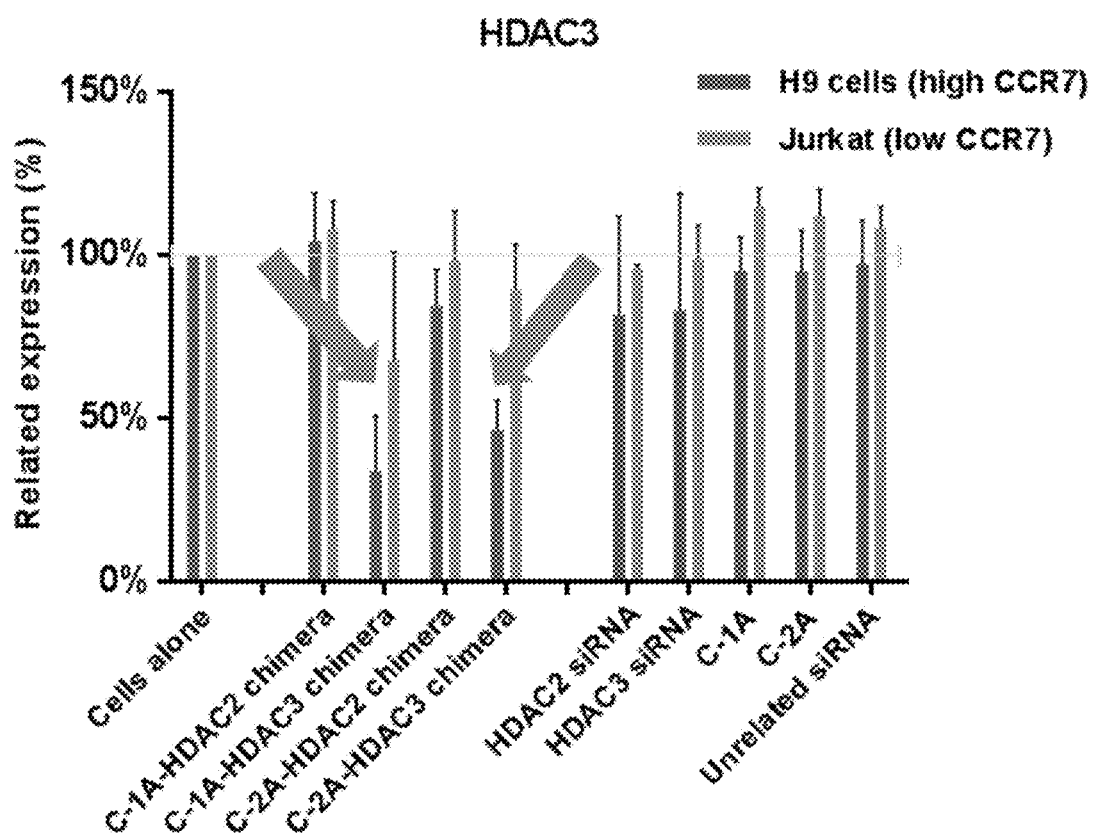
FIG. 10 shows that CCR7 aptamer-siRNA conjugates mediated specific gene silencing in CCR7-expressing H9 cells, while non-CCR7-conjugated siRNA had no silencing effect in the assay.

CCR7 aptamers, C-1A and C-2A, were conjugated to HDAC2 siRNA and HDAC3 siRNA respectively. The silencing effects of the CCR7 aptamers alone, siRNAs alone, and the CCR7 aptamer-siRNA conjugates were tested in H9 cells having a high expression level of CCR7 and Jurkat cells having a low expression level of CCR7. As demonstrated by FIG. 10, CCR7 aptamer-siRNA conjugates demonstrated specific gene silencing effects in CCR7 expressing H9 cells, while the aptamers alone and non-CCR7-conjugated siRNAs did not show silencing effects.

Example 3: Gene Activating Effects of CCR7 Aptamer-Small RNA Nano-Conjugates

Figure 11:
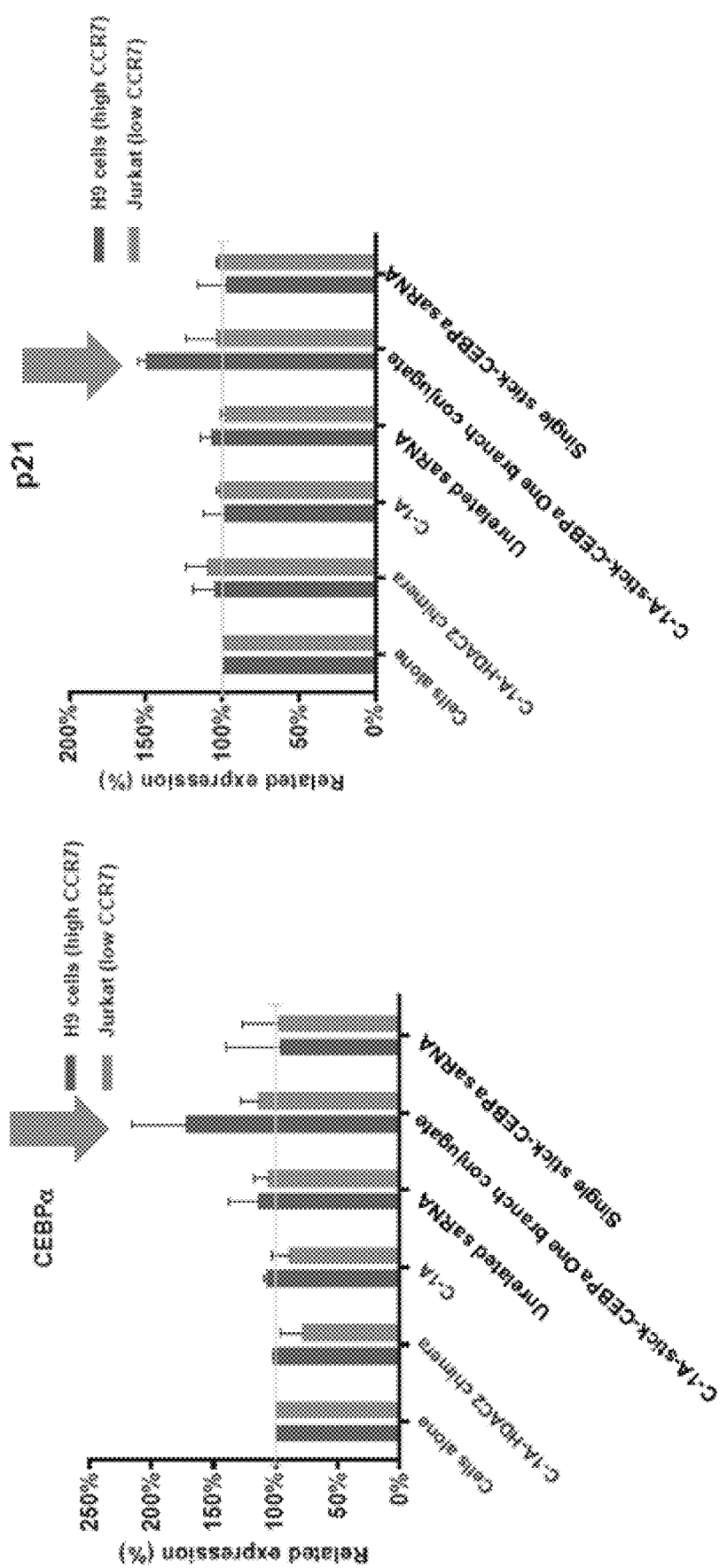
FIG. 11 shows that CCR7 aptamer-saRNA conjugate mediated specific gene activation in CCR7-expressing H9 cells, while other constructs did not.

CCR7 aptamer, C-1A, was conjugated to C/EBPα saRNA and an unrelated saRNA respectively. The activating effects of the CCR7 C-1A aptamer alone, saRNAs alone, and the CCR7 aptamer-saRNA conjugates were tested in H9 cells having a high expression level of CCR7 and Jurkat cells having a low expression level of CCR7. Two dose of 400 nM of experimental RNAs were directly incubated with H9 cells or Jurkat cells at day 1 and day 2. At 48 hour post-incubation, total RNA was isolated for qRT-PCR analysis. As demonstrated by FIG. 11, only the CCR7 aptamer-C/EBPα saRNA conjugate demonstrated specific gene activating effects on the target gene C/EBPα (left) and its downstream gene p21 (right) in CCR7-expressing H9 cells, while other constructs did not show activating effects. The results suggested that CCR7 aptamer-based RNA nano-conjugates selectively delivered saRNA into CCR7 expressing cells, therefore specifically upregulating the target gene as well as its downstream gene.

Figure 12:
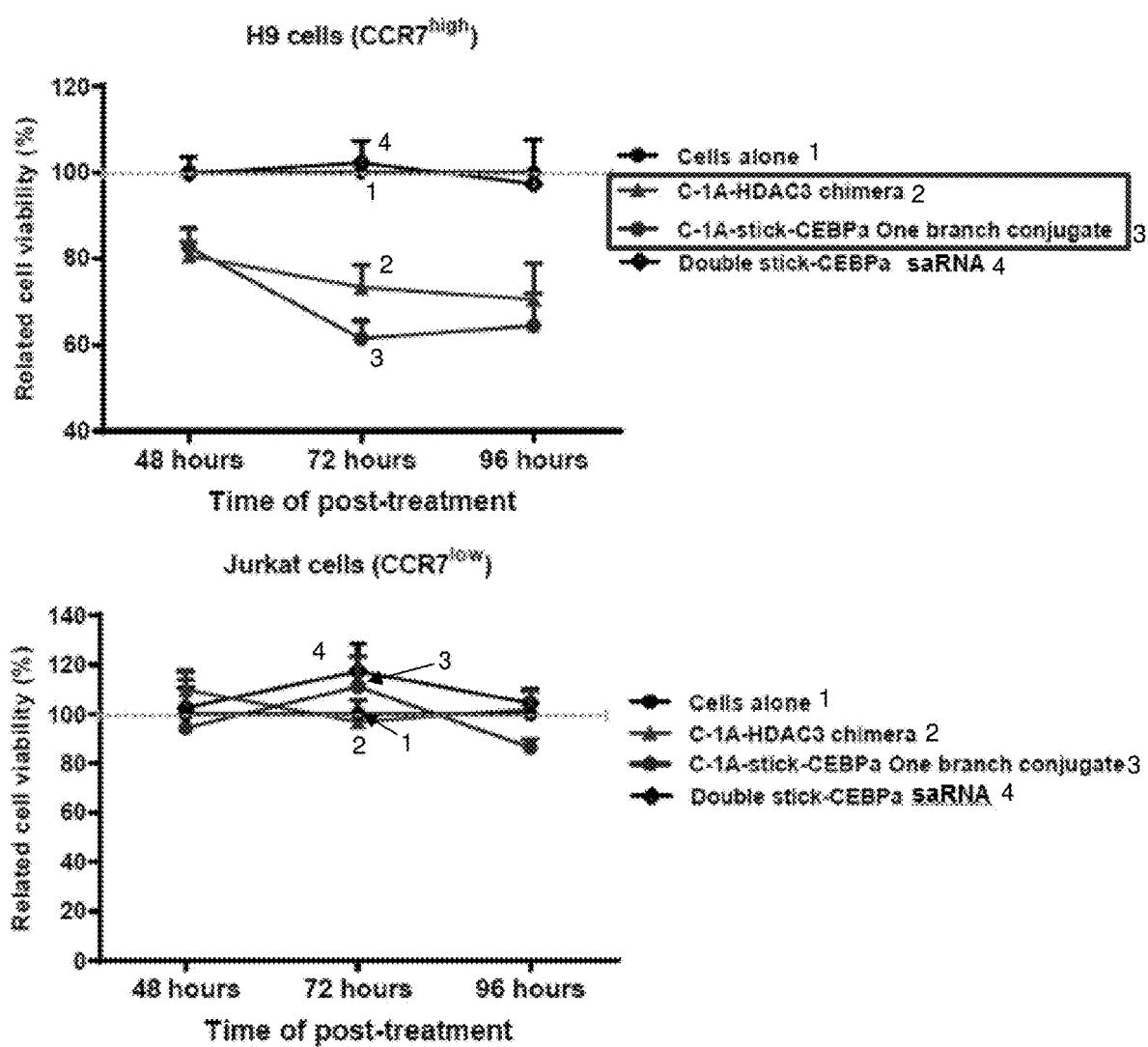
FIG. 12 shows that CCR7 aptamer-C/EBPα saRNA conjugate inhibited cell proliferation in CCR7-expressing H9 cells but not in Jurkat cells.

Example 4: Inhibition of Cell Proliferation by CCR7 Aptamer-Small RNA Nano-Conjugates CCR7 aptamer, C-1A, was conjugated to C/EBPα saRNA, and the effects of the conjugate on cell proliferation were tested in H9 cells expressing a high level of CCR7 and in Jurkat cells expressing a low level of CCR7. Two dose of 400 nM of experimental RNAs were directly incubated with H9 cells or Jurkat cells at day 1 and day 2. At 48 hour post-incubation, MTS assay was conducted to determine the cell viability. As demonstrated by FIG. 12, the CCR7 aptamer-C/EBPα saRNA conjugate inhibited specific cell proliferation by inhibiting about 40% cell proliferation in H9 cells which expressed a high level of CCR7 but had no effect on Jurkat cells which expressed a low level of CCR7. 72 hours post-treatment showed the best suppression on cell proliferation. Collectively, it was demonstrated that CCR7 aptamer-based RNA nano-conjugates selectively delivered saRNA into CCR7 expressing cells, therefore specifically inhibiting the target cells proliferation.

REFERENCES

The references listed below, and all references cited in the specification are hereby incorporated by reference in their entireties, as if fully set forth herein.

1 Tuerk, C. & Gold, L. Systematic evolution of ligands by exponential enrichment: RNA ligands to bacteriophage T4 DNA polymerase. *Science* 249, 505-510 (1990).
2 Ellington, A. D. & Szostak, J. W. In vitro selection of RNA molecules that bind specific ligands. *Nature* 346, 818-822 (1990).
3 Darmostuk, M., Rimpelova, S., Gbelcova, H. & Ruml, T. Current approaches in SELEX: An update to aptamer selection technology. *Biotechnol Adv* 33, 1141-1161, doi: 10.1016/j.biotechadv.2015.02.008 (2015).
4 Keefe, A. D., Pai, S. & Ellington, A. Aptamers as therapeutics. *Nature reviews. Drug discovery* 9, 537-550, doi: 10.1038/nrd3141 (2010).
5 Sundaram, P., Kurniawan, H., Byrne, M. E. & Wower, J. Therapeutic RNA aptamers in clinical trials. *Eur J Pharm Sci* 48, 259-271, doi: S0928-0987 (12) 00414-9 [pii] 10.1016/j.ejps.2012.10.014 (2013).
6 Zhou, J. & Rossi, J. J. Cell-type-specific, Aptamer-functionalized Agents for Targeted Disease Therapy. *Mol Ther Nucleic Acids* 3, e169, doi: 10.1038/mtna.2014.21 (2014).
7 Guo, K. T., Ziemer, G., Paul, A. & Wendel, H. P. CELL-SELEX: Novel perspectives of aptamer-based therapeutics. *International journal of molecular sciences* 9, 668-678 (2008).

The invention claimed is:

1. A cell-type specific aptamer-small molecule conjugate comprising:
   an aptamer that specifically binds CCR7, the aptamer selected from the group consisting of C-1A (SEQ ID NO: 1), C-2A (SEQ ID NO: 2), DD9-9 (SEQ ID NO: 3), and C-6 (SEQ ID NO: 4), and
   a small molecule conjugated to the aptamer, wherein the small molecule is not an aptamer.

2. The aptamer-small molecule conjugate of claim 1, wherein the aptamer is an RNA molecule.

3. The aptamer-small molecule conjugate of claim 1, wherein the aptamer is chemically modified in-SELEX or post-SELEX.

4. The aptamer-small molecule conjugate of claim 1, wherein the aptamer is chemically modified by replacing the 2' position with either a fluoro-(F), amino-($NH_2$), or O-methyl ($OCH_3$) group, and by capping the 3' end with inverted thymidine.

5. The aptamer-small molecule conjugate of claim 1, wherein the small molecule is selected from the group consisting of an saRNA, an siRNA, an shRNA, an miRNA, a chemotherapeutic agent, and a toxin.

6. The aptamer-small molecule conjugate of claim 5, wherein the saRNA targets CCAAT/enhancer-binding protein-α.

7. The aptamer-small molecule conjugate of claim 1, wherein the aptamer is conjugated to the small molecule via one or more linkers.

8. The aptamer-small molecule conjugate of claim 7, wherein the linker is a nucleotide linker or a polycarbon linker.

9. The aptamer-small molecule conjugate of claim 1, wherein the aptamer is conjugated to the small molecule via a sticky bridge comprising a complementary sequence.

10. A method for treating a cancer patient comprising administering a therapeutically effective amount of a therapeutic composition, wherein the therapeutic composition comprises a CCR7 aptamer or a conjugate of a CCR7 aptamer and a small molecule, wherein the small molecule is not an aptamer,
   wherein the CCR7 aptamer is selected from the group consisting of C-1A (SEQ ID NO: 1), C-2A (SEQ ID NO: 2), DD9-9 (SEQ ID NO: 3), and C-6 (SEQ ID NO: 4).

11. The method of claim 10, wherein the aptamer is an RNA molecule.

12. The method of claim 10, wherein the aptamer is chemically modified in-SELEX or post-SELEX.

13. The method of claim 10, wherein the aptamer is chemically modified by replacing the 2' position with either a fluoro-(F), amino-($NH_2$), or O-methyl ($OCH_3$) group, and by capping the 3' end with inverted thymidine.

14. The method of claim 10, wherein the small molecule is selected from the group consisting of an saRNA, an siRNA, an shRNA, an miRNA, a chemotherapeutic agent, and a toxin.

15. The method of claim 10, wherein the patient suffers from breast cancer, melanoma, non-small cell lung cancer, prostate cancer, chronic lymphocytic leukemia (CLL), non-Hodgkin's lymphoma (NHL), or T-cell leukemia.

* * * * *

SEQUENCE LISTING

```
<160> NUMBER OF SEQ ID NOS: 5

<210> SEQ ID NO 1
<211> LENGTH: 61
<212> TYPE: RNA
<213> ORGANISM: Artificial Sequence
<220> FEATURE:
<223> OTHER INFORMATION: C-1A aptamer

<400> SEQUENCE: 1
```

```
gggaggacga ugcgguuucg uccugaguuc guguccucgu cugugcagac gacucgcccg    60
a                                                                    61

<210> SEQ ID NO 2
<211> LENGTH: 61
<212> TYPE: RNA
<213> ORGANISM: Artificial Sequence
<220> FEATURE:
<223> OTHER INFORMATION: C-2A aptamer

<400> SEQUENCE: 2
gggaggacga ugcggaauuc gucaaagucg uuuauuucgu cugugcagac gacucgcccg    60
a                                                                    61

<210> SEQ ID NO 3
<211> LENGTH: 61
<212> TYPE: RNA
<213> ORGANISM: Artificial Sequence
<220> FEATURE:
<223> OTHER INFORMATION: DD9-9 aptamer

<400> SEQUENCE: 3
gggaggacga ugcggugccg cacauuaguc ucgguugcc cacgccagac gacucgcccg     60
a                                                                    61

<210> SEQ ID NO 4
<211> LENGTH: 61
<212> TYPE: RNA
<213> ORGANISM: Artificial Sequence
<220> FEATURE:
<223> OTHER INFORMATION: C-6 aptamer

<400> SEQUENCE: 4
gggaggacga ugcgguccau cgucucuuau cgucucuugu cgcgccagac gacucgcccg    60
a                                                                    61

<210> SEQ ID NO 5
<211> LENGTH: 31
<212> TYPE: DNA
<213> ORGANISM: Artificial Sequence
<220> FEATURE:
<223> OTHER INFORMATION: C-6 aptamer

<400> SEQUENCE: 5
gggaggacga tgcggcagac gactcgcccg a                                   31
```